Figure 1:
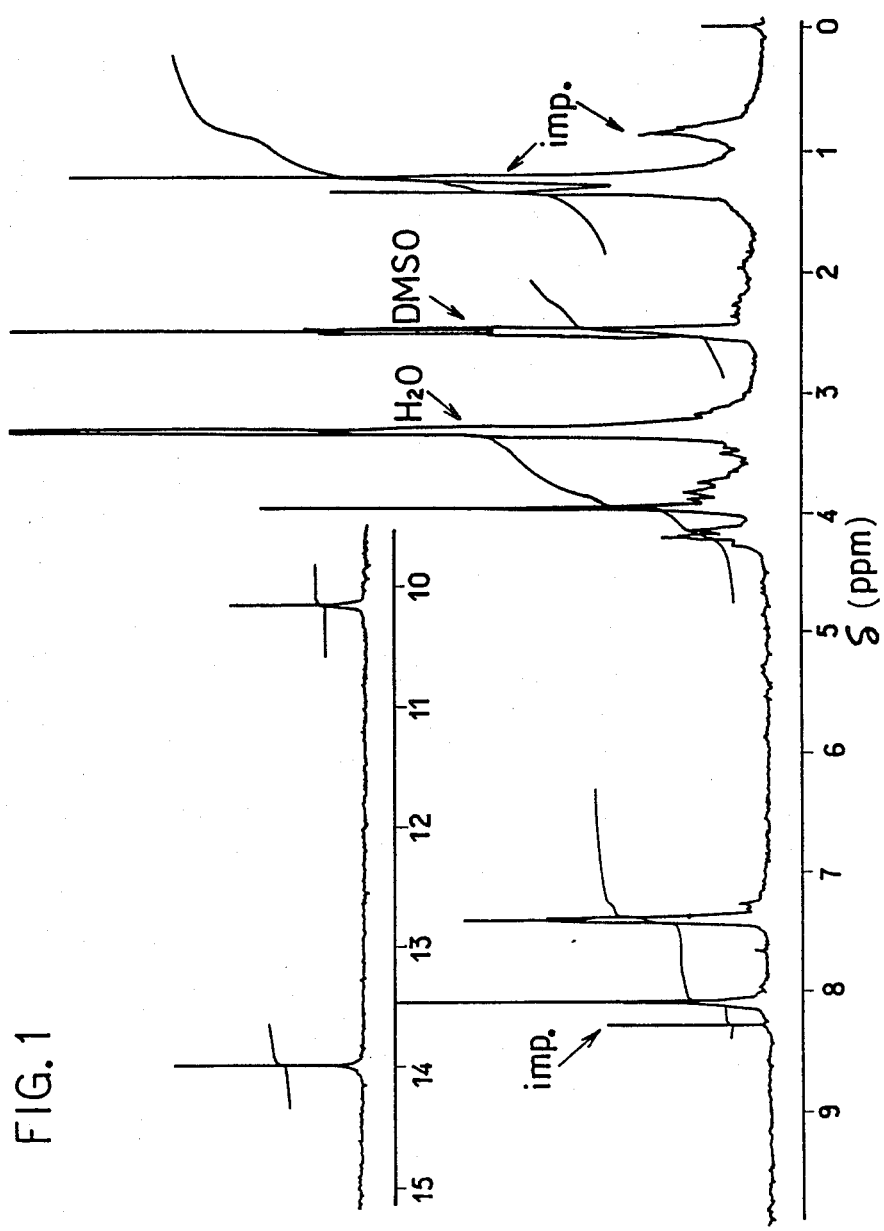

United States Patent [19]

Chang-qing et al.

[11] Patent Number: 4,866,069
[45] Date of Patent: Sep. 12, 1989

[54] SUBSTANCE 4181-2 AND ITS DERIVATIVES HAVING ANTI-LEUKEMIA ACTIVITY

[75] Inventors: Qi Chang-qing; Tian Jie, both of Beijing, China; Teruyoshi Marunaka, Tokushima, Japan; Yuji Yamada, Tokushima, Japan; Ichiro Yamawaki, Tokushima, Japan; Toshio Ohtani, Tokushima, Japan; Yoshinori Minami, Naruto, Japan; Hitoshi Saito, Tokushima, Japan

[73] Assignee: Taiho Pharmaceutical Company, Limited, Tokyo, Japan

[21] Appl. No.: 252,722

[22] Filed: Oct. 3, 1988

Related U.S. Application Data

[62] Division of Ser. No. 048,297, May 11, 1987, Pat. No. 4,814,449.

[30] Foreign Application Priority Data

May 16, 1986 [JP] Japan ............................. 61-113323
May 16, 1986 [JP] Japan ............................. 61-113324

[51] Int. Cl.[4] ............... A61K 31/33; C07D 491/14; C07D 491/147
[52] U.S. Cl. ............................. 514/279; 514/908; 546/36
[58] Field of Search ............................. 514/279, 908

[56] References Cited

U.S. PATENT DOCUMENTS 4,814,449 3/1989 Chang-qing et al. ............... 546/36

FOREIGN PATENT DOCUMENTS 54801 6/1982 European Pat. Off. .
102897 6/1982 Japan .
05023 8/1987 World Int. Prop. O. .

OTHER PUBLICATIONS

Omura et al., CA106-47255 (1987), "Structure of Cervinomycin; a Novel Antianaerobic Antibiotic".
Nakajawa et al., CA106-814327 (1987), "Enhanced Anti-microbial Activity of Acetyl Derivatives of Cervinomycin".
Nakajawa et al., CA107-217314t(1987), "Structure of Cervinomycin, a Novel Xanthone Antibiotic Active Against Anaeroben and Mycoplasma".
The Journal of Antibiotics, vol. XXXV, No. 6 (1982), pp. 645–652.
Proceedings of 106th Congress of Japanes Phamacological Society held on 4/2-4/1986, p. 207,45-10-3, by Nakagawa et al., p. 489, 3E 10-3, by Shimizu et al.
Omura et al., J.A.C.S. 108(1986) pp. 6088–6089.
Omura et al., The Journal of Antibiotics, vol. XL, No. 3, (1987), pp. 301–308.

*Primary Examiner*—Cecilia Shen
*Attorney, Agent, or Firm*—Armstrong, Nikaido, Marmelstein, Kubovcik & Murray

[57] ABSTRACT

Disclosed are a compound of the general formula

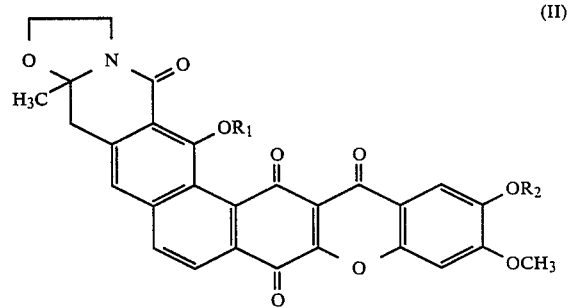

(II)

wherein $R_1$ and $R_2$ are the same or different and each represents a hydrogen atom, an alkyl group or an acyl group, process for the production thereof and use thereof. The compounds have an antitumor activity, and those wherein both of $R_1$ and $R_2$ represent a hydrogen atom or an acyl group are novel compounds.

4 Claims, 6 Drawing Sheets

SUBSTANCE 4181-2 AND ITS DERIVATIVES HAVING ANTI-LEUKEMIA ACTIVITY

This is a division, of application Ser. No. 048,297 filed May 11, 1987, now U.S. Pat. No. 4,814,449.

The present invention relates to novel Substance 4181-2 and its derivatives, a method for production thereof and use thereof.

Substance 4181-2 according to the present invention is a novel compound of the formula

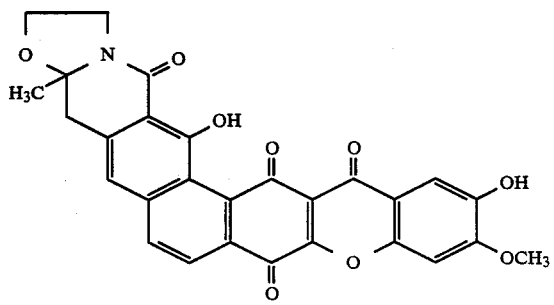

which has not been described in the literature.

The research undertaken by us into the substances which various microorganisms elaborate and the properties of such substances led to the finding that culturing a certain microorganism of the genus Streptomyces yields the above-mentioned Substance 4181-2 and that this substance not only has a broad antibicrobial spectrum covering gram-positive and gram-negative bacteria and various fungi but also has excellent antitumor activity. Furthermore, we have found that the novel derivatives obtainable by substituting both the two hydrogen atoms of two hydroxyl groups of Substance 4181-2 with acyl groups have similar antitumor and other activities.

The present invention, therefore, provides compounds of general formula

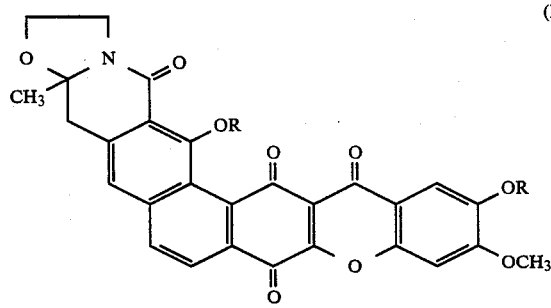

in which R is a hydrogen atom or an acyl group.

We have further found that compounds obtainable by chemical modification of one or both of the two hydrogen atoms represented by R in Substance 4181-2 with an alkylating agent and/or an acylating agent also possess antitumor activity. Therefore, the present invention provides an antitumor composition containing an effective amount of a compound of the general formula

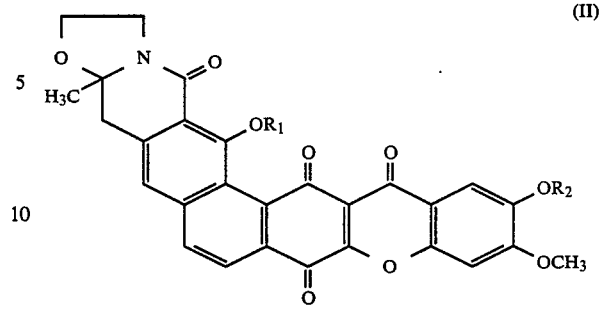

wherein $R_1$ and $R_2$ are the same or different and each represents a hydrogen atom, an alkyl group or an acyl group, together with a pharmaceutically acceptable carrier.

The present invention further provides a method for treating tumors in mammals including man comprising administering an effective amount of a compound of general formula (II) to the mammals.

In this specification and particularly referring to general formula (I) and (II) except where noted otherwise, the term "acyl" is used to refer to an acyl group containing 2 to 5 carbon atoms, such as acetyl, propionyl, butyryl, valeryl, etc., and the term "alkyl" is used to refer to a straight-chain or branched alkyl group containing 1 to 5 carbon atoms, such as methyl, ethyl, propyl, isopropyl, butyl, isobutyl, t-butyl, pentyl and t-amyl.

In the Proceedings (published March 10, 1986) of the 106th Congress of The Japanese Pharmacological Society held on April 2nd to 4th, 1986 at pages 207 and 489, there is described a compound similar to the compound of general formula (I) according to the present invention. This compound, represented by the following structural formula

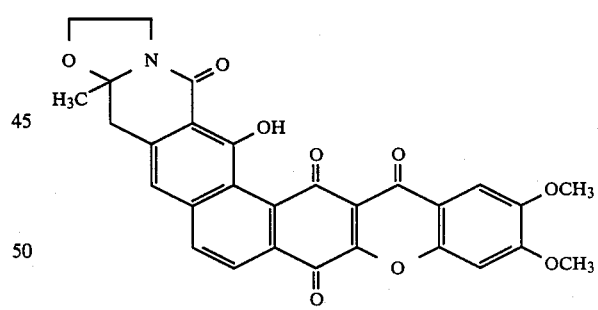

is referred to as cervinomycin $A_2$. The compound obtainable by reducing its xanthone nucleus is referred to as cervinomycin $A_1$. The Proceedings further describe the compounds corresponding to cervinomycin $A_2$ in which the hydrogen atom of its hydroxyl group has been substituted by a methyl group or an acetyl group, and cervinomycin $A_1$ triacetate corresponding to cervinomycin $A_1$ in which the hydrogen atom of each of its 3 hydroxyl groups has been substituted by an acetyl group. Further, Japanese Unexamined Patent Publication (Kokai) No. 102897/1982, European Patent Application published under No. 54801 and The Journal of Antibiotics, Vol. XXXV, No. 6, June, 1982 describe the above-mentioned cervinomycin $A_1$ and $A_2$, not by structural formula but by their physico-chemical properties. However, the above literature merely state that cervinomycin $A_1$ and $A_2$ and their derivatives mentioned above have antimicrobial activity but do not even suggest at all the fact that these compounds have antitumore activity.

The method for production of compounds of general formulas (I) and (II) is described below.

Of the compounds of general formulas (I) and (II), the compound in which the substituent R in the formula (I) or the substituents $R_1$ and $R_2$ in the formula (II) are hydrogen atoms (i.e., Substance 4181-2) can be produced by cultivation of microorganisms. Thus, a strain of microorganism capable of producing Substance 4181-2 is cultured under suitable conditions and the resulting Substance 4181-2 is harvested from the mycelial cakes or the culture filtrate.

The acyl derivative or alkyl derivative of Substance 4181-2 can be synthesized by subjecting Substance 4181-2 to the per se conventional acylation or alkylation reaction. For example, an acyl derivative of Substance 4181-2 can be produced by reacting Substance 4181-2 with an acyl halide or an acid anhydride in the presence or absence of an organic solvent and in the presence or absence of an organic base such as ammonia, pyridine, triethylamine, etc. or an inorganic base such as metal hydroxides (e.g. sodium hydroxide, potassium hydroxide, etc.), inorganic salts (e.g. sodium carbonate, potassium hydrogen carbonate, etc.), and metal oxides (e.g. silver oxide, etc.) at a temperature of about $-50°$ C. to about $100°$ C., preferably between room temperature and the boiling point of the solvent used. The alkyl derivative of Substance 4181-2 can be produced by reacting Substance 4181-2 with an alkyl halide or an alkyl ester of sulfunic acid, sulfonic acid or phosphoric acid under the same conditions as above.

With respect to the above acylating agents, examples of the acyl halide are those having 2-5 carbon atoms, such as acetyl chloride, acetyl bromide, propionyl chloride, propionyl bromide, butyryl chloride, butyryl bromide, valeryl chloride, valeryl bromide and the like, and examples of the acid anhydride are anhydrides of fatty acids having 2-5 carbon atoms, such as acetic anhydride, propionic anhydride, butyric anhydride, valeric anhydride and the like.

With respect to the above alkylating agent, examles of alkyl halide are those having 1-5 carbon atoms, such as methyl iodide, methyl bromide, methyl chloride, ethyl iodide, ethyl bromide, propyl chloride, propyl bromide, isopropyl iodide, butyl iodide, isobutyl bromide, sec-butyl chloride, tert-butyl bromide, pentyl bromide, isoamyl chloride, tert-amyl chloride, 2-bromopentane and the like, and examples of the alkyl esters are those of sulfuric acid, such as dimethyl sulfate, diethyl sulfate, those of sulfonic acids, such as methyl p-toluenesulfonate, ethyl p-toluenesulfonate, methyl benzenesulfonate, ethyl benzenesulfonate, butyl p-toluenesulfonate, butyl benzenesulfonate, propyl p-toluenesulfonate and the like, and those of phosphoric acid, such as methyl phosphate, ethyl phosphate, propyl phosphate, n-butyl phosphate, tert-butyl phosphate and the like.

When the acylating or alkylating agent is used in an amount of about 1 mole per mole of Substance 4181-2, the reaction generally gives as a main product the mono-acyl or mono-alkyl derivative thereof, which, if desired, can be further reacted with an acylating or alkylating agent to give a compound of the formula (II) wherein one of $R_1$ and $R_2$ is an acyl group and the other is an alkyl group or wherein both of $R_1$ and $R_2$ are the same or different alkyl or acyl group. On the other hand, when the acylating or alkylating agent is used in an amount of at least about 2 moles, preferably about 2 to about 10 moles per mole of Substance 4181-2, the reaction predominantly gives a compound of the formula (II) wherein $R_1$ and $R_2$ are the same and represent an acyl or alkyl group.

As said organic solvent, hydrocarbons such as hexane, halogenated hydrocarbons such as chloroform, ethers such as ethyl ether and dioxane, ketones such as acetone, aromatic hydrocarbons such as benzene and toluene, aprotic polar solvents such as nitromethane, dimethylformamide and dimethyl sulfoxide, for instance, can be used singly or in admixture. If necessary, the above-mentioned bases can also be used as the solvent as well.

The strain of microorganism to be employed in the production of Substance 4181-2 may be any strain of microrganism that is able to produce Substance 4181-2. As an example, Strain 4181 of the genus Streptomyces which was isolated by the present inventors can be mentioned. This Strain 4181 is a microorganism of the genus Streptomyces which the present inventors isolated from a soil sample collected in Emei-Shan, Sichuansheng of the People's Republic of China and has been deposited at Fermentation Research Institute, Agency of Industrial Science and Technology at 1-3, Higashi 1-chome, Yatabe-machi, Tsukuba-gun, Ibaraki-ken, 305, Japan under the accession number of FERM BP-1010 under Budapest Treaty as of April 2, 1986. The bacteriological characteristics of Strain 4181 are as follows.

Microbiological Characteristics (a) Morphology
Branching of the sporophore: monopodial
Spore chain morphology: Straight (Rectus Flexibilis) (cylindrical spores)
Number of spores: 10 or more per chain
Spore surface: Smooth
Size of spore: $0.8-1.0 \times 1.1-1.5$ $\mu$m
Flagellum: none
Sporangium: none
Position of sporophore: aerial mycelium
Sclerotium: none (b) Cultural characteristics on various media are given in Table 1.

TABLE 1

| Medium | Growth | Aerial mycelium | Reverse side | Production of soluble pigment |
|---|---|---|---|---|
| Sucrose nitrate agar | Good | Light gray | Dark olive | None |
| Glucose-asparagine agar | Moderate | Substantially not produced or sparse white | Pale Yellow | None |
| Glycerin-asparagine agar (ISP-5) | Moderate | Light yellowish gray -light gray | Dark olive brown | None |
| Starch-inorganic salt agar (ISP-4) | Poor | Not produced or | Colorless | None |

TABLE 1-continued

| Medium | Growth | Aerial mycelium | Reverse side | Production of soluble pigment |
|---|---|---|---|---|
| Tyrosine agar (ISP-7) | Good | sparse white White - light gray | Dark olive | None |
| Oatmeal agar (ISP-3) | Good | White - light gray | Olive | None |
| Yeast-malt extract agar (ISP-2) | Moderate | Whitish light gray | Pale yellowish tan | None |
| Nutrient agar | Moderate | Not formed | Pale Yellow | None |
| Bennett's agar | Moderate | Not formed | Pale yellow-yellowish tan | None |
| Gauze No. 1 agar | Good | Light gray | Dark olive | None |

(c) Physiological characteristics
(1) Temperature range for growth: Good growth at 26°–30° C.; no growth at 40° C. and higher temperatures
(2) Liquefaction of gelatin (glucose-peptone gelatin): positive (more than 3 weeks)
(3) Coagulation of milk: negative Peptonization of milk: positive
(4) Production of melanoid pigment: negative on tyrosine agar (ISP-7) and peptone yeast extract iron agar (ISP-6)
(5) Production of hydrogen sulfide: negative
(6) Hydrolysis of starch (starch agar): positive
(7) Reduction of nitrate: negative
(8) Decomposition of cellulose: positive
(d) Utilization of carbon sources (Pridham-Gottlieb agar, ISP-9)

The strain grows well utilizing all of the following carbohydrates: L-arabinose, D-xylose, D-glucose, D-fructose, inositol, L-rhamnose, raffinose, D-mannitol, sucrose, starch, D-mannose, maltose, D-sorbitol, cellulose and inulin.

(e) Whole cell composition

Analysis by the method of Becker et al (Applied Microbiology 12, 421-423, 1964) revealed that the whole cell hydrolysate of this strain contained LL-diaminopimelic acid and a small amount of glycine.

In view of the above bacteriological characteristics of Strain 4181 that it forms aerial mycelia having many spore chains from the substrate mycelium, its cell constituent diaminopimelic acid is the LL-form, and it does not have flagella or sporangia, it is clear that this strain is a microorganism belonging to the genus Streptomyces. Accordingly, this strain was named Streptomyces species 4181.

Substance 4181-2 according to the present invention can be produced, for example by culturing said Streptomyces species 4181 or a mutant thereof in a suitable medium.

The cultural method may be any of the methods commonly used for the cultivation of microorganisms but it is generally preferably to cultivate A Substance 4181-2-producing strain by aerobic culture such as shaking culture or submerged culture using a liquid medium. The culture medium is one containing the nutrients which the strain can utilize. In this sense, any of synthetic, semi-synthetic and natural media can be employed. As carbon sources, glucose, sucrose, fructose, glycerol, dextrin, starch, molasses, corn steep liquor, organic acids and so on can be used singly or in combination. As nitrogen sources, organic nitrogenous materials such as Pharmamedia (trademark, product of TRADERS OIL COMPANY, U.S.A., containing 60% of protein and the balance being ash, fiber and the like), peptone, meat extract, yeast extract, soybean flour, casein, amino acids, urea, etc. and inorganic nitrogen sources such as sodium nitrate, ammonium sulfate and so on can be used singly or in combination. If necessary, minerals such as sodium salts, potassium salts, magnesium salts, phosphates, heavy metal salts and so on may also be incorporated in the medium.

If marked foaming occurs during the fermentation, suitable amounts of an antifoam such as vegetable oils, e.g. soybean oil, linseed oil, etc., higher alcohols such as octadecanol, tetradecanol, heptadecanol, etc., various silicone compounds, and so on can be added.

The pH of the medium is preferably maintained slightly acidic or near neutral. Since the 4181-2-producing strain is generally considered to grow at temperatures between about 20° C. and about 37° C., the incubation is generally conducted at about 20° to 37° C. and preferably at about 27° to 30° C. When the liquid medium is used, Substance 4181-2 is accumulated by conducting the cultivation for 2–5 days.

Of course, the optimum set of cultural conditions should be selected from the foregoing conditions in accordance with the particular Substance 4181-2 producer used, its characteristics, and other conditions. The isolation of Substance 4181-2 produced in the culture can be performed by the conventional procedure for isolating microbial metabolites. For example, solvent extraction, pH adjustment, crystallization and other techniques can be used singly or in a suitable combination and in a suitable sequence.

Substance 4181-2 is accumulated both in the culture medium and in the mycelial cake. Therefore, the medium is first centrifuged or filtered and the mycelial cake is treated with a solvent such as acetone, methanol or a mixture thereof to extract Substance 4181-2. On the other hand, the supernatant or filtrate is treated with a water-immiscible solvent such as ethyl acetate, chloroform, butanol or a mixture thereof to extract Substance 4181-2 into the organic layer and, after addition of sodium sulfate to the organic layer for dehydration, the solvent is distilled off under reduced pressure to give a crude extract containing Substance 4181-2. If necessary, pH adjustment with hydrochloric acid or sulfuric acid or by addition of brine can be conducted for effective extraction.

For purification, the conventional purification procedures for lipophilic low molecular weight substances can be employed. Thus, various adsorption chromatographic procedures using such adsorbents as silica gel, alumina, macroporous non-ionic adsorbent resin, etc. can be utilized. Particularly preferred is silica gel chromatography using chloroform-methanol as an eluent. For further purification, if required, the above chromatographic procedure can be repeated or conducted in combination with recrystallization from a solvent such as chloroform, methanol or acetone, and/or other techniques. By these procedures, a high-purity grade of Substance 4181-2 can be isolated.

The antitumor composition containing Substance 4181-2 or a derivative thereof as an active component in accordance with the present invention can be administered in various dosage forms of the treatment of tumors in man and animals. These dosage forms may be oral dosage forms, injections, suppositories, and so on and each can be manufactured by the established pharmaceutical procedures. In the preparation of a solid composition for oral administration, Substance 4181-2 or a derivative thereof can be formulated with an excipient with or without addition of a binder, disintegrating agent, lubricant, color, savor, aroma, etc. and processed into tablets, coated tablets, granules, powders, capsules and so on in the per se known manner. For the production of parenteral preparations, Substance 4181-2 or a derivative thereof can be formulated with a pH adjusting agent, buffer, stabilizer, isotonizing agent, local anesthetic and so on and processed into injections for administration by the subcutaneous, intramuscular, intravenous or other route. For the preparation of suppositories, Substance 4181-2 or a derivative thereof is formulated with a suitable suppository base with or without addition of a surfactant and processed into suppositories in the per se known manner.

As examples of the excipient used in the manufacture of tablets, capsules, granules or powders, there may be mentioned lactose, sucrose, starch, talc, magnesium stearate, crystalline cellulose, methylcellulose, carboxymethylcellulose, glycerol, sodium alginate, gum arabic and so on. Examples of said binder include polyvinyl alcohol, polyvinyl ether, ethylcellulose, gum arabic, shellac, sucrose, and so on. Examples of said lubricating agent include magnesium stearate, talc and so on. The color, flavor, disintegrating agent and other auxiliaries may be those used commonly in the art. Tablets may be coated by the established pharmaceutical procedure.

The suppository based used in the manufacture of suppositories include, among others, such oleaginous bases as cacao butter, polyethylene glycol, lanolin, fatty acid triglycerides, Witepsol (trademark of Dynamite Nobel, mono, di or triglyceride) and so on.

The amount of Subtsance 4181-2 or a derivative thereof in the pharmaceutical composition according to the present invention varies with the patient's condition, the particular dosage from and other factors, but generally it is about 0.04 to 4 mg per unit oral dosage form, about 0.004 to 2 mg per injection, and about 0.04 to 4 mg per suppository. The daily dosage also varies with the patient's condition and other factors but generally may be in the range of about 0.004 to 12 mg for adult humans.

The present invention contemplates the use of Substance 4181-2, or a derivative thereof, alone, in mixtures thereof, or in combination with known anti-cancer drugs to treat tumors in mammals. The types of tumors to be treated, especially in humans, would include tumors of the lung, colon, rectum, breast, ovaries, head and neck, liver, and stomach.

The production of compounds according to the present invention is described in the examples which appear hereinafter. In these examples, the identification of the compound according to the invention was made by bioassay and bioautography using *Staphylococcus aureus* 209P, *Sarcina lutea* ATCC 9341, etc. as test organisms or by the investigation of cytotoxic effect on the cultured cell line derived for human nasopharyngeal carcinoma (KB cells).

EXAMPLE 1

Production of Substance 4181-2 (Compound 1)

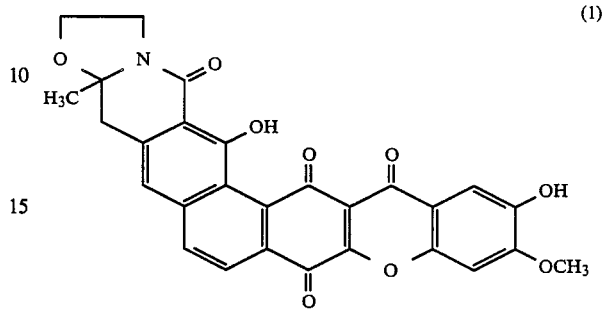

A 500 ml conical flask was charged with 100 ml of a medium composed of 0.1% of glucose, 0.1% of polypeptone, 0.3% of meat extract, 0.5% of yeast extract, 2.4% of soluble starch and 0.3% of calcium carbonate (pH 7.0). After sterilization, the medium was inoculated with a loopful of Streptomyces species 4181 (FERM BP-1010) and incubated on a rotary shaker at 27° C. for 48 hours (180 r.p.m., 10 cm in amplitude). Then, a 500 ml conical flask was charged with 100 ml of a medium composed of 4.0% of glycerol, 1.0% of Pharmamedia, 0.2% of sodium chloride, 0.2% of magnesium sulfate, and 0.3% of calcium carbonate (pH 7.0). After sterilization, the 5% of above seed culture was added, followed by fermentation on a rotary shaker at 272° C. for 96 hours. After completion of cultivation, the culture broth (7.4 l, pH 7.4) was centrifuged and filtered and the mycelial cake was extracted with 3 portions of methanol (about 1 l each). The extract was concentrated under reduced pressure and the residue was extracted with 3 portions of ethyl acetate (0.3 l each) with stirring. The both filtrate was adjusted to pH 3 with diluted hydrochloric acid and extracted with 3 portions of ethyl acetate (0.8 l each). The extracts were pooled and, then, combined with the mycelial extract obtained above, and after washing with water, the combined extract was dehydrated over anhydrous sodium sulfate and concentrated under reduced pressure to give a brown oil (6.42 g). This oil was dissolved in ethyl acetate (0.3 l) followed by addition of n-hexane (0.5 l). The resulting precipitate was filtered and evaporated to dryness to give a reddish brown crude powder (801 mg) containing Substance 4181-2.

The above powder was dissolved in chloroform (about 10 ml) and adsorbed on a silica gel chromatographic column (Merck, Kieselguhr, 5.9×19 cm). After the column was washed with chloroform (1.4 l), elution was carried out with 3.9 l of chloroform-methanol (20:1). The fractions containing Substance 4181-2 were collected and the solvent was distilled off. The residue was recrystallized from chloroform-acetone and dried to give a reddish orange powder (83 mg).

m.p. >260° C. (decomposition)

Figure 2:
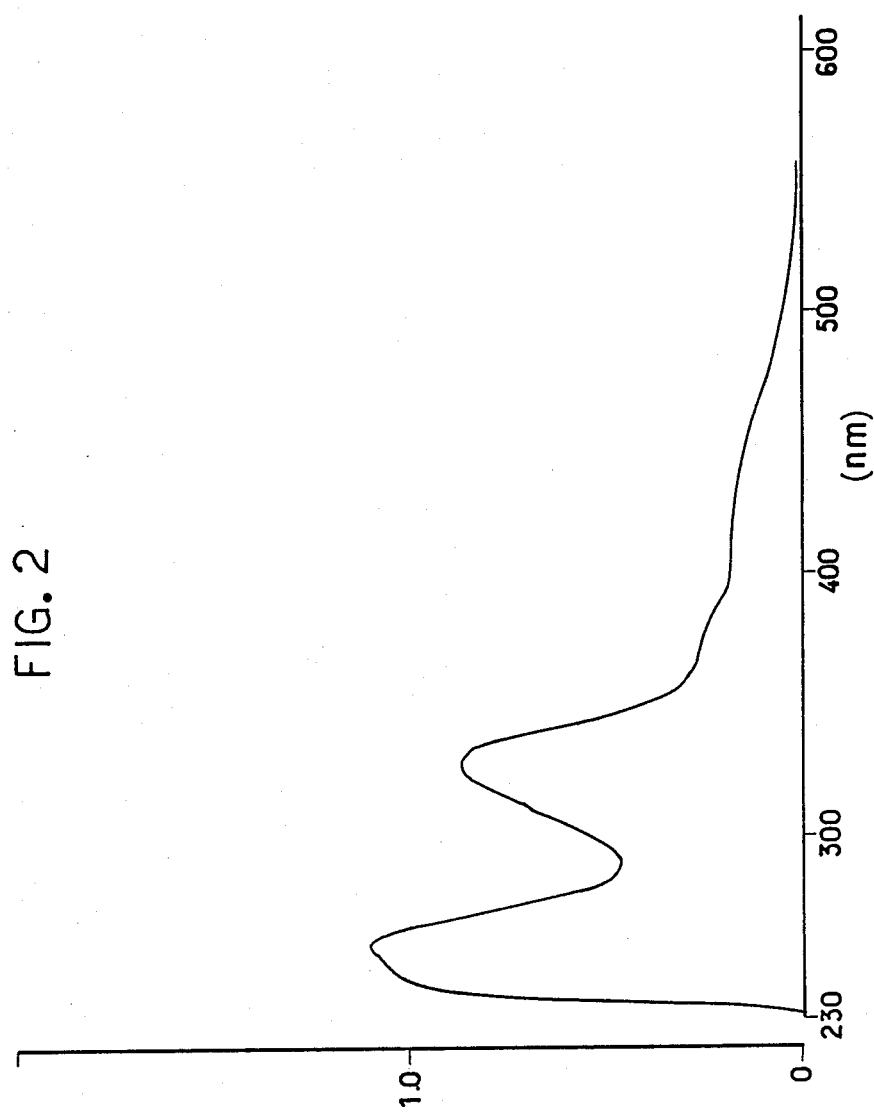
Figure 3:
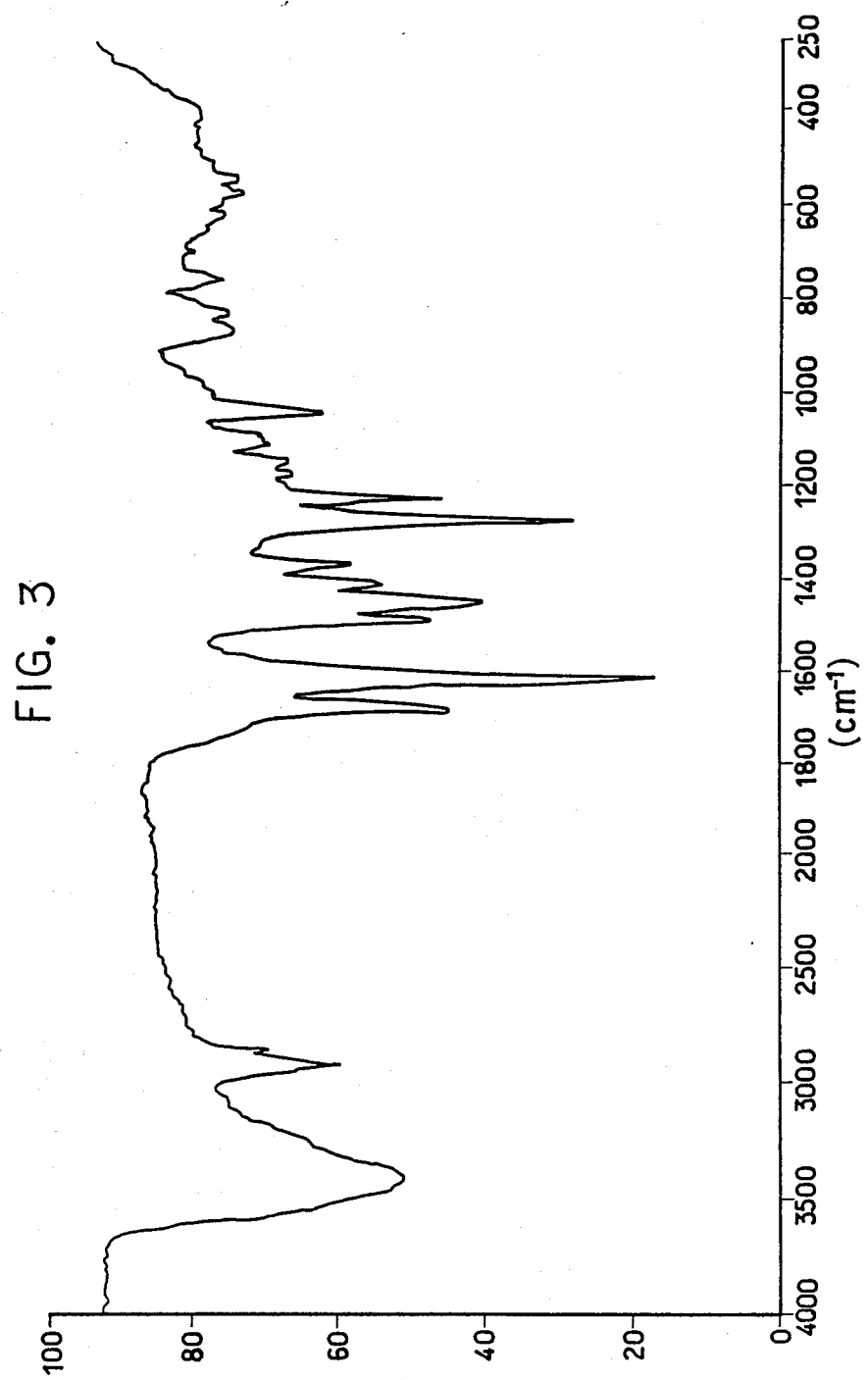

The $^1$H-NMR spectrum (in DMSO-$d_6$), ultraviolet absorption spectrum (in CHCl$_3$) and infrared absorption spectrum (KBr) of Compound 1 are shown in FIGS. 1, 2 and 3, respectively.

EXAMPLE 2

Synthesis of the diacetyl derivative of Substance 4181-2 (Compound 2)

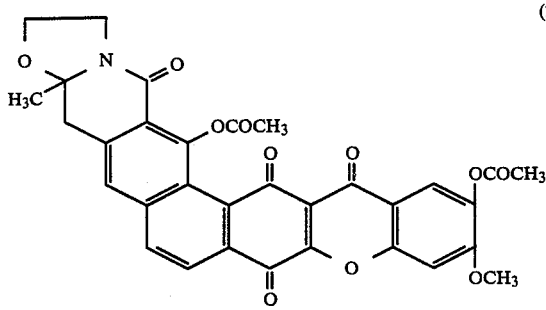

(2)

Under ice-cooling, acetic anhydride (7.5 ml) was added dropwise to a solution of Substance 4181-2 (29 mg) in a mixture of chloroform (15 ml) and pyridine (15 ml) and the mixture is stirred at room temperature overnight. The reaction mixture was concentrated and the residue was dissolved in chloroform and subjected to silica gel column chromatography (Merch, Kieselguhr, 5.9×19 cm). Then, elution was carried out with chloroform-methanol (50:1) and the eluate was concentrated to dryness to give the title compound (28 mg, yield 83%).

m.p. 208°–212° C. (decomposition)

Figure 4:
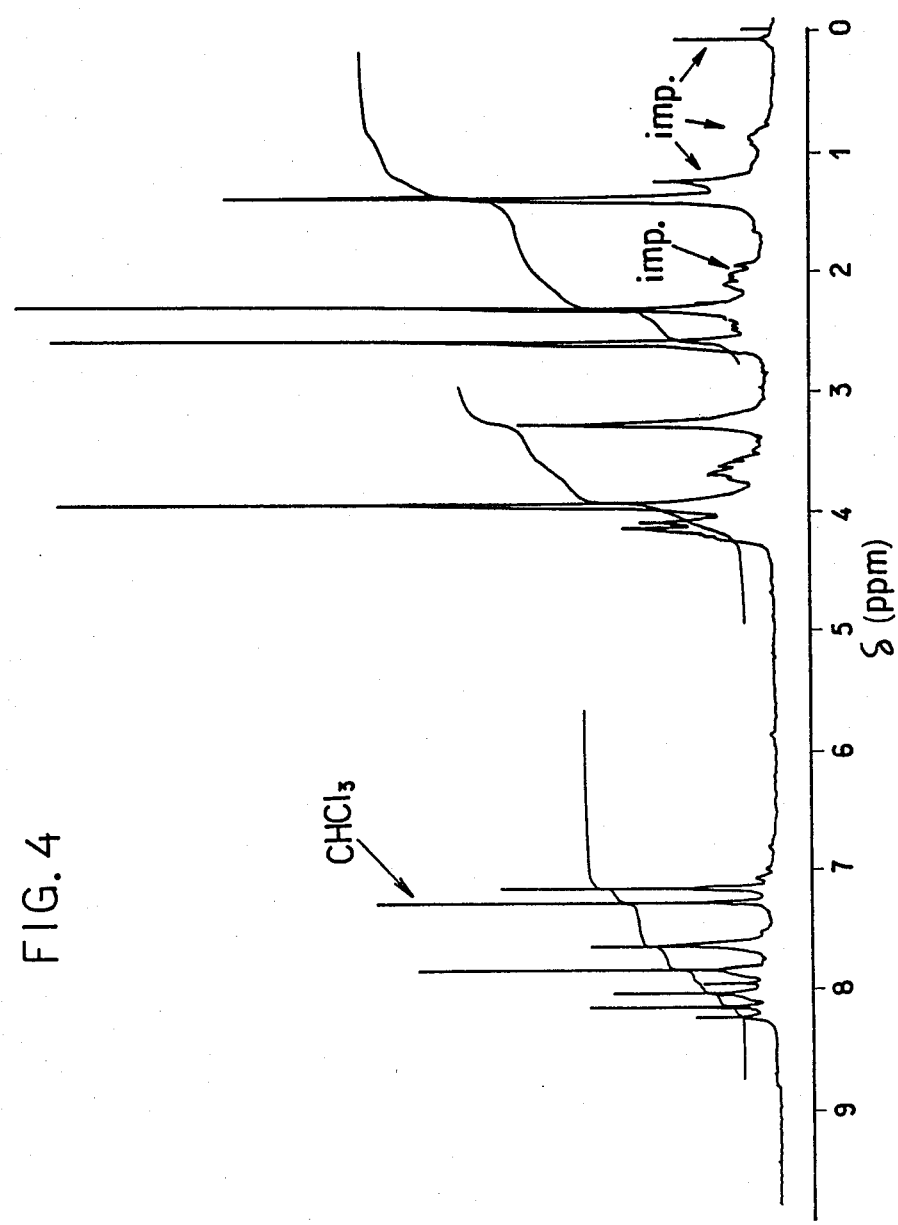

The $^1$H-NMR spectrum of Compound 2 in CDCl$_3$ is shown in FIG. 4.

EXAMPLE 3

Synthesis of the monomethyl derivative of Substance 4181-2 (Compound 3)

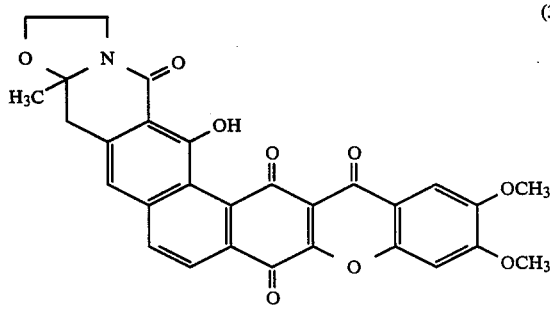

(3)

In 100 ml of a mixture of chloroform and methanol (10:1) was dissolved Substance 4181-2 (100 mg) followed by addition of silver oxide (45.2 mg), and then, methyl iodide (27.6 mg). The mixture was stirred overnight and, the reaction mixture was filtered. The filtrate was concentrated, redissolved in chloroform and subjected to silica gel column chromatography (Merck, Kieselguhr, 5.9×19 cm) and elution was carried out with chloroform. The eluate was concentrated to dryness to give the title compound (20 mg, yield 19.5%).

m.p. >300° C. (decomposition)

Figure 5:
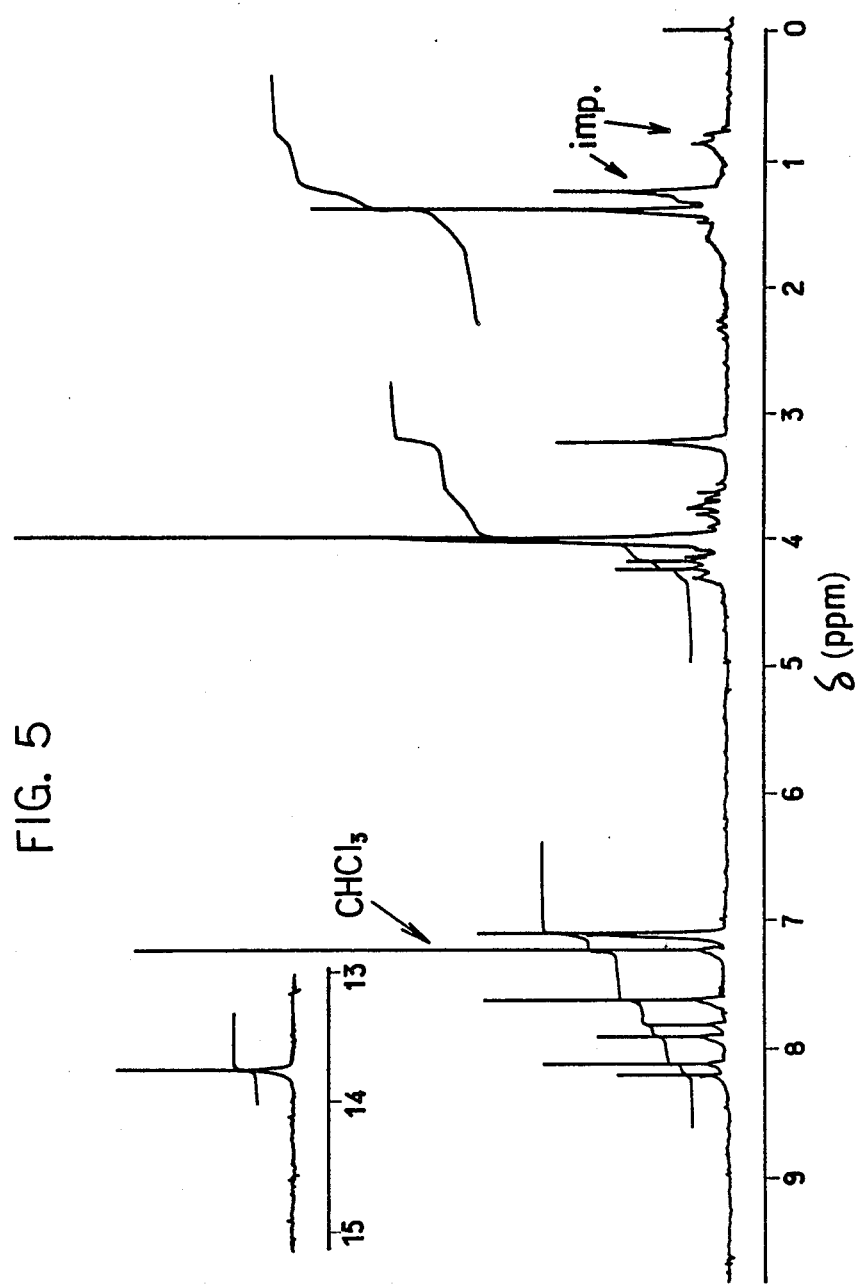

The $^1$H-NMR spectrum of Compound 3 in CDCl$_3$ is shown in FIG. 5.

EXAMPLE 4

Synthesis of the monomethyl monoacetyl derivative of Substance 4181-2 (Compound 4)

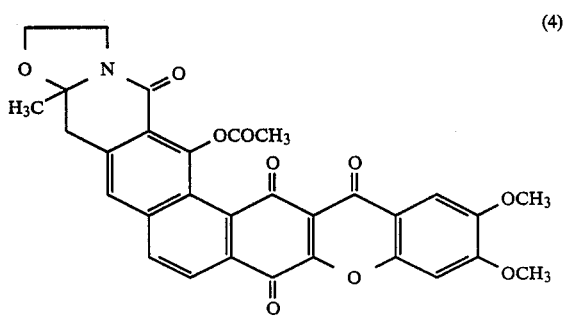

(4)

The methyl ether (40 mg) obtained in Example 3 was dissolved in chloroform (20 ml) - pyridine (20 ml), and with ice-cooling, 10 ml of acetic anhydride was added dropwise. The reaction mixture was worked up in the same manner as Example 2 to give the title compound (35 mg, yield 81.6%).

m.p. 220°–225° C. (decomposition)

Figure 6:
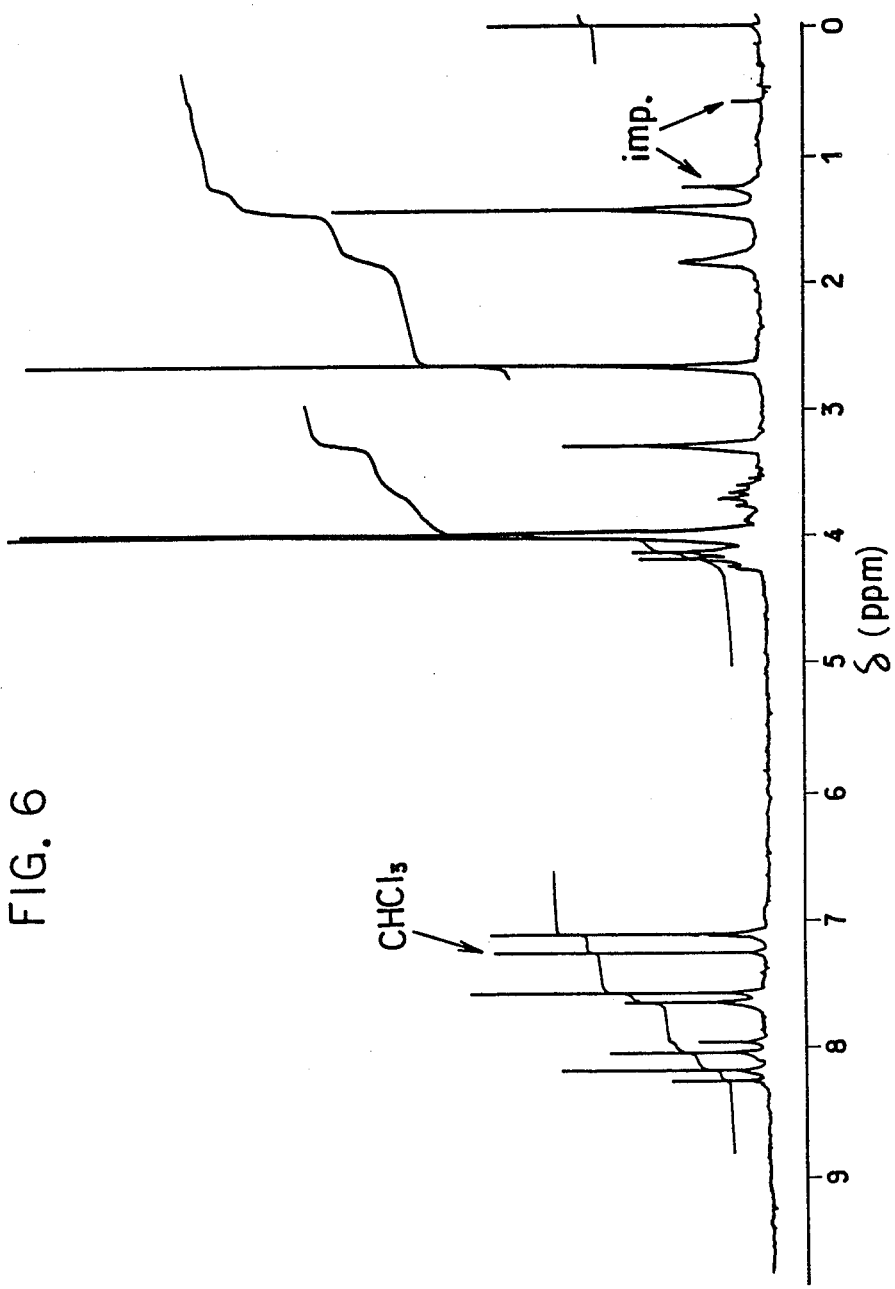

The $^1$H-NMR spectrum of Compound 4 in CDCl$_3$ is shown in FIG. 6.

Substance 4181-2 and its acyl and/or alkyl derivatives represented by general formula (I) or (II) not only have a broad antimicrobial spectrum of microorganisms including gram-positive bacteria, gram-negative bacteria and fungi but also have excellent antitumor activity. The results of pharmacological tests conducted for elucidating the antibacterial, antifungal and antitumor activites of these compounds are shown below.

PHARMACOLOGICAL TESTS

1. Antimicrobial spectrum

The antibacterial and antifungal spectra of Substance 4181-2 were investigated. Using nutrient agar medium for gram-positive and gram-negative bacteria and Sabouraud's agar medium for fungi, the minimal inhibitory concentration (MIC) was determined by a two-fold serial dilution method. The antimicrobial spectrum of Substance 4181-2 are shown in Table 2.

TABLE 2

| Antimicrobial Spectrum of Substance 4181-2 | | | |
|---|---|---|---|
| Test organism | MIC(μg/ml) | Test organism | MIC(μg/ml) |
| *Staphylococcus aureus* 209P | 0.2 | *Candida albicans* IFO 1061 | 0.39 |
| *Micrococcus flavus* ATCC 10240 | 0.2 | *Saccharomyces delbrueckii* IAM 12236 | 1.56 |
| *Bacillus subtilis* ATCC 6633 | 0.2 | *Aspergillus niger* IFO 6341 | 3.13 |
| *Escherichia coli* B IFO 13168 | 1.56 | *Penicillium notatum* IFO 4640 | 1.56 |
| *Proteus vulgalis* IFO 3045 | 0.39 | *Trichophyton mentagrophytes* IFO 5466 | 0.78 |
| *Klebsiella pneumoniae* ATCC 10031 | 3.13 | | |

TABLE 2-continued

| Antimicrobial Spectrum of Substance 4181-2 | | | |
|---|---|---|---|
| Test organism | MIC(µg/ml) | Test organism | MIC(µg/ml) |
| *Pseudomonus fluorescens* IFO 12180 | 0.2 | | |

2. Antitumor activity

The antitumor activity of Substance 4181-2 and its derivatives was evaluated in terms of the increase in life span. One $\times 10^6$ of leukemia P388 cells were intraperitoneally injected to $BDF_1$ mice. Each group consisted of 6 mice. On the following day, each of Compounds 1–4, suspended in 0.2% solution of Tween 80 in physiological saline, was administered intraperitoneally and the survival time in days was determined. The results are shown in Table 3. The percent increase in survival time was calculated by means of the following formula.

Percent increase in survival time $= ((D/D_0) - 1) \times 100$ wherein $D_0$ stands for the mean survival time (days) in the untreated group and D stands for the mean survival time (days) in the treated group.

TABLE 3

| Life span-prolonging effect in mouse leukemia | | | |
|---|---|---|---|
| Compound | Dose (mg/kg) | Mean survival time (days) | % Increase in survival time |
| Untreated control | — | 9.3 ± 0.8 | — |
| Compound 1 | 3 | 18.0 ± 1.4 | 94 |
| Compound 2 | 3 | 14.8 ± 0.8 | 59 |
| Compound 3 | 3 | 15.2 ± 1.7 | 63 |
| Compound 4 | 3 | 14.2 ± 0.8 | 53 |

3. Acute toxicity study

Male mice of ddY strain (body weight 25 g) were used. Each of Compounds 1–4 was suspended in 0.2% solution of Tween 80 in physiological saline and administered intraperitoneally to the animals. The $LD_{50}$ values (mg/kg) were determined by the up-and-down method. The results are shown in Table 4.

TABLE 4

| Compound No. | $LD_{50}$ (mg/kg) |
|---|---|
| 1 | ≧40 |
| 2 | ≧40 |
| 3 | ≧40 |
| 4 | ≧40 |

Formulation Examples using the compounds of the invention are shown below.

| Formulation Example 1 Tablet | |
|---|---|
| Compound 1 | 4 mg |
| Lactose | 43 mg |
| Corn starch | 50 mg |
| Crystalline cellulose | 50 mg |
| Hydroxypropylcellulose | 15 mg |
| Talc | 2 mg |
| Magnesium stearate | 2 mg |
| Ethylcellulose | 30 mg |
| Fatty acid glycerin ester | 2 mg |
| Titanium dioxide | 2 mg |
| Per tablet | 200 mg |

Tablets were manufactured using the above components in the above-mentioned proportions.

| Formulation Example 2 Granule | |
|---|---|
| Compound 2 | 2 mg |
| Mannitol | 738 mg |
| Corn starch | 100 mg |
| Crystalline cellulose | 100 mg |
| Hydroxypropylcellulose | 50 mg |
| Talc | 10 mg |
| Per packet | 1000 mg |

Granules were prepared using the above components in the above-mentioned proportions.

| Formulation Example 3 Fine granule | |
|---|---|
| Compound 3 | 4 mg |
| Mannitol | 716 mg |
| Corn starch | 100 mg |
| Crystalline cellulose | 100 mg |
| Hydroxypropylcellulose | 70 mg |
| Talc | 10 mg |
| Per packet | 1000 mg |

Fine granules were prepared using the above components in the above-mentioned proportions.

| Formulation Example 4 Capsule | |
|---|---|
| Compound 4 | 1 mg |
| Lactose | 99 mg |
| Corn starch | 97 mg |
| Crystalline cellulose | 50 mg |
| Talc | 2 mg |
| Magnesium stearate | 1 mg |
| Per capsule | 250 mg |

Capsules were prepared using the above components in the above-mentioned proportions.

| Formulation Example 5 Injection | |
|---|---|
| Compound 1 | 0.04 mg |
| Distilled water for injection | q.s. |
| Per ampule | 2 ml |

An injectable solution was prepared using the above components in the above-mentioned quantities.

| Formulation Example 6 Suppository | |
|---|---|
| Compound 2 | 1 mg |
| Witepsol ® W-35 | 1499 mg |
| Per suppository container | 1500 mg |

Suppositories were prepared using the above components in the above-mentioned proportions.

What is claimed is:

1. An anti-leukemia composition comprising an effective amount of a compound

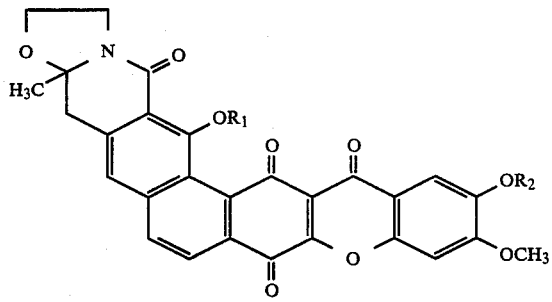

wherein $R_1$ and $R_2$ are the same or different and each represents a hydrogen atom, an alkyl group or an acyl group, as an active ingredient, and a pharmaceutically acceptable carrier.

2. The anti-leukemia composition of claim 1 wherein $R_1$ and $R_2$ each represents a hydrogen atom.

3. A method for treatment of leukemia in mammalian animals which comprises administering to said mammalian animals an effective amount of a compound of the formula

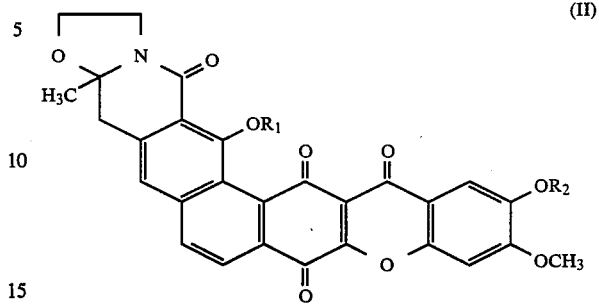

(II)

wherein $R_1$ and $R_2$ are the same or different and each represents a hydrogen atom, an alkyl group or an acyl group.

4. The method of claim 3 wherein $R_1$ and $R_2$ each is a hydrogen atom.

* * * * *